(12) United States Patent
Watanabe et al.

(10) Patent No.: US 8,345,090 B2
(45) Date of Patent: Jan. 1, 2013

(54) FLUOROSCOPY APPARATUS HAVING AN IMAGE CORRECTION SECTION

(75) Inventors: Toshiaki Watanabe, Tokyo (JP); Yasushige Ishihara, Tokyo (JP)

(73) Assignee: Olympus Corporation, Tokyo (JP)

( * ) Notice: Subject to any disclaimer, the term of this patent is extended or adjusted under 35 U.S.C. 154(b) by 400 days.

(21) Appl. No.: 12/726,549

(22) Filed: Mar. 18, 2010

(65) Prior Publication Data

US 2010/0245619 A1  Sep. 30, 2010

(30) Foreign Application Priority Data

Mar. 24, 2009 (JP) ................................ 2009-072848

(51) Int. Cl.
*A62B 1/04* (2006.01)
(52) U.S. Cl. ............... 348/65; 348/68; 348/73; 600/109
(58) Field of Classification Search .................... 348/65, 348/68, 73
See application file for complete search history.

(56) References Cited

U.S. PATENT DOCUMENTS

| 7,798,955 B2 * | 9/2010 | Ishihara et al. ............... 600/101 |
| 2002/0093563 A1 * | 7/2002 | Cline et al. ..................... 348/65 |
| 2010/0245550 A1 * | 9/2010 | Ishihara ........................ 348/68 |
| 2010/0245551 A1 * | 9/2010 | Morita ........................... 348/68 |
| 2010/0245552 A1 * | 9/2010 | Higuchi ......................... 348/68 |
| 2011/0074942 A1 * | 3/2011 | Endo et al. ..................... 348/68 |

FOREIGN PATENT DOCUMENTS

| JP | 62-247232 | 10/1987 |
| JP | 2001-224549 | 8/2001 |

* cited by examiner

*Primary Examiner* — Ngoc-Yen Vu
(74) *Attorney, Agent, or Firm* — Scully Scott Murphy & Presser, PC (57) ABSTRACT

A fluoroscopy apparatus includes an illumination portion irradiating an observation target with illumination light; a fluorescence image acquisition device acquires fluorescence emitted from an observation target to acquire a fluorescence image; a fluorescence image-acquisition optical system forms an image of the observation target using the fluorescence; a reference-light image acquisition device acquires returning light from the observation region to acquire a reference image; a reference-light image-acquisition optical system forms an image using the returning light; and an image correction section corrects the fluorescence image by the reference image, wherein the product of an pixel density of the reference-light image acquisition device and the image-forming magnification of the reference-light image-acquisition optical system is less than the product of the pixel density of the fluorescence image acquisition device and the image-forming magnification of the fluorescence image-acquisition optical system.

9 Claims, 5 Drawing Sheets

FLUOROSCOPY APPARATUS HAVING AN IMAGE CORRECTION SECTION

BACKGROUND OF THE INVENTION

1. Field of the Invention

The present invention relates to fluoroscopy apparatus.

This application is based on Japanese Patent Application No. 2009-072848, the content of which is incorporated herein by reference.

2. Description of Related Art

It has hitherto been known that in fluoroscopy apparatus such as fluorescence endoscopes, the irradiation intensity of excitation light in the observation region varies depending on the angle and distance of the excitation light with which the observation target is irradiated, and the intensity of fluorescence generated varies. In order to correct such variation in the fluorescence intensity, fluoroscopy apparatus is known in which the effect of distance and angle is corrected by performing division by a reference image acquired in the same observation region (e.g., a reflected-light image or the like) (e.g., see Japanese Unexamined Patent Application, Publication No. Sho 62-247232).

Furthermore, a method is known in which the resolution is intentionally reduced by low-pass filtering an image acquired as a reference image (e.g., see Japanese Unexamined Patent Application, Publication No. 2001-224549).

However, the reference image includes information other than information about the distance and angle, for example, image information of blood vessel structures or edges in a case where the observation target is biological tissue. Therefore, if correction is performed by simply using the reference image, in some cases, it is not possible to perform quantitative correction over the entire image, which results in degraded image quality.

Furthermore, in a case where it is necessary to perform image processing for removing high-frequency components on all the pixels of the acquired image information, the processing speed becomes slow.

BRIEF SUMMARY OF THE INVENTION

It is an object of the present invention to provide a fluoroscopy apparatus with which unwanted information included in a reference image is suppressed and a fluorescence image including quantitative intensity information can be acquired quickly by simple processing regardless of the angle and distance of excitation light.

An aspect of the present invention provides a fluoroscopy apparatus including an illumination portion that irradiates an observation target with illumination light including excitation light; a fluorescence image acquisition device that acquires fluorescence emitted from a specified observation region of the observation target to acquire a fluorescence image; a fluorescence image-acquisition optical system that forms an image of the observation target using the fluorescence on an image-acquisition surface of the fluorescence image acquisition device; a reference-light image acquisition device that acquires returning light returning from the observation region to acquire a reference image; a reference-light image-acquisition optical system that forms an image of the observation target using the returning light on an image-acquisition surface of the reference-light image acquisition device; and an image correction section that corrects the fluorescence image acquired by the fluorescence image acquisition device by using the reference image acquired by the reference-light image acquisition device, wherein the product of an effective pixel density of the reference-light image acquisition device and the image-forming magnification of the reference-light image-acquisition optical system is less than the product of the pixel density of the fluorescence image acquisition device and the image-forming magnification of the fluorescence image-acquisition optical system.

According to the above aspect, when the observation target is irradiated with illumination light including excitation light, emitted from the illumination portion, a fluorescent material contained in the observation target is excited to generate fluorescence. Fluorescence generated in the specified observation region is acquired as a fluorescence image by the fluorescence image acquisition device via the fluorescence image-acquisition optical system. Returning light from the same observation region is acquired as a reference image by the reference-light image acquisition device via the reference-light image-acquisition optical system. Then, the image correction sections correct the fluorescence image by using the reference image acquired by acquiring an image of the same observation target. Accordingly, variation in the fluorescence intensity, which depends on the distance and angle of the illumination light, is corrected, whereby a quantitative fluorescence image is acquired.

In this case, since the product of an effective pixel density of the reference-light image acquisition device and the image-forming magnification of the reference-light image-acquisition optical system is set to be less than the product of the pixel density of the fluorescence image acquisition device and the image-forming magnification of the fluorescence image-acquisition optical system, the reference image acquired by the reference-light image acquisition device has a resolution lower than the resolution of the fluorescence image acquired by the fluorescence image acquisition device. Therefore, information about the surface condition, etc. of the observation target is not contained in the reference image. By performing correction using the reference image, it is possible to suppress inclusion of information about the surface condition, etc. of the observation target in the corrected fluorescence image. Accordingly, it is possible to acquire a fluorescence image including precise and quantitative intensity information.

In the above aspect, preferably, the image correction section divides the fluorescence image by the reference image.

Accordingly, it is possible to acquire a highly quantitative fluorescence image by simple calculation.

In the above aspect, the reference-light image acquisition device may acquire the reference image at a pixel density lower than the actual pixel density by pixel binning.

Accordingly, it is possible to readily acquire a reference image having a lower resolution by using the reference-light image acquisition device which is capable of acquiring an image having a higher resolution. Therefore, since it is possible to acquire a reference image by using an image acquisition device that is capable of acquiring an image having a higher resolution, there is no need to provide a special image acquisition device dedicated to reference images.

In the above aspect, the reference-light image acquisition device may acquire a reference image acquired with pixel binning and a returning-light image acquired without pixel binning in a time division manner by switching pixel binning on and off.

Accordingly, by switching pixel binning on and off, a reference image and an image for observation having a higher resolution than the reference image are acquired in a time division manner. Therefore, it is possible to sequentially acquire an image for observation and a reference image for correcting a fluorescence image for the same observation region.

In the above aspect, the fluoroscopy apparatus including the illumination portion that irradiates the observation target simultaneously with white light and excitation light as illumination light after the illumination portion irradiates the observation target simultaneously with white light and excitation light as illumination light, a light-collecting lens that collects returning light returning from the observation target; a first splitting portion that splits the returning light collected by the light-collecting lens into fluorescence and white light; a second splitting portion that further splits the white light split by the first splitting portion; a white-light image-acquisition optical system that focuses one of the white light beams split by the second splitting portion; and a white-light image acquisition device having an image-acquisition surface at a focal position of the white-light image-acquisition optical system, the fluorescence split by the first splitting portion may be guided to the fluorescence image acquisition device, and the other white light beam split by the second splitting portion may be guided to the reference-light image acquisition device via the reference-light image-acquisition optical system.

Accordingly, when the observation target is irradiated simultaneously with the white light and excitation light, at the observation target, an internal fluorescent material is excited to generate fluorescence, and the white light is reflected at the surface of the observation target. The fluorescence and white light that return from the observation target are collected by the light-collecting lens, and then the fluorescence split by the first splitting portion is acquired as a fluorescence image by the fluorescence image acquisition device via the fluorescence image-acquisition optical system.

On the other hand, the white light split by the first splitting portion is further split into two by the second splitting portion, and one of the white light beams is acquired as a white-light image by the white-light image acquisition device via the white-light image-acquisition optical system. The other white light beam is guided to the reference-light image acquisition device via the reference-light image-acquisition optical system and acquired as a reference image having a low resolution. Thus, it is possible to simultaneously acquire a white-light image for displaying the surface condition of the observation target and a precisely corrected fluorescence image.

Another aspect of the present invention provides a fluoroscopy apparatus including an illumination portion that irradiates an observation target with illumination light including excitation light; a fluorescence image acquisition device that acquires fluorescence emitted from a specified observation region of the observation target to acquire a fluorescence image; a fluorescence image-acquisition optical system that forms an image of the observation target using the fluorescence on an image-acquisition surface of the fluorescence image acquisition device; a returning-light image acquisition device that acquires returning light returning from the observation region; a returning-light image-acquisition optical system that forms an image of the observation target using the returning light on an image-acquisition surface of the returning-light image acquisition device; a reference-image generating unit that generates a reference image by decimating pixels of a returning-light image acquired by the returning-light image acquisition device; and an image correction section that corrects the fluorescence image acquired by the fluorescence image acquisition device by using the reference image generated by the reference-image generating unit.

In the above aspect, when the observation target is irradiated with illumination light including excitation light, fluorescence generated inside the observation target is acquired as a fluorescence image by the fluorescence image acquisition device, and white light, etc. reflected at the surface of the observation target is acquired by the returning-light image acquisition device. Then, the reference-image generating unit decimates pixels of the returning-light image acquired by the returning-light image acquisition device to generate a reference image having a low resolution. By correcting the fluorescence image by using the generated reference image, it is possible to acquire a quantitative fluorescence image in which variation in the fluorescence intensity, which depends on the distance and angle of the illumination light, is corrected.

In the above aspect, the reference-image generating unit may generate the reference image by reading out pixel information at intervals of one or more pixels of the returning-light image acquired by the returning-light image acquisition device.

Accordingly, it is possible to generate a reference image having a low resolution simply by decimating pixels when reading out pixel information.

In the above aspect, the reference-image generating unit may control the timing at which the returning-light image is read out when generating the reference image.

Accordingly, it is possible to perform control so that the timing at which the returning-light image is read out is delayed and to generate a reference image having a low resolution simply by decimating pixels when reading out pixel information.

The reference-image generating unit may switch the timing at which the returning-light image is read out to generate, in a time division manner, a reference image at delayed read-out timing and a returning-light image at advanced readout timing.

Accordingly, it is possible to alternately acquire a reference image having a low resolution and an image for observation having a high resolution.

According to the present invention, an advantage is afforded in that it is possible to suppress unwanted information included in a reference image and to quickly acquire a fluorescence image including quantitative intensity information by simple processing regardless of the angle and distance of excitation light.

DETAILED DESCRIPTION OF THE INVENTION

A fluoroscopy apparatus 1 according to an embodiment of the present invention will be described below with reference to the drawings.

Figure 1:
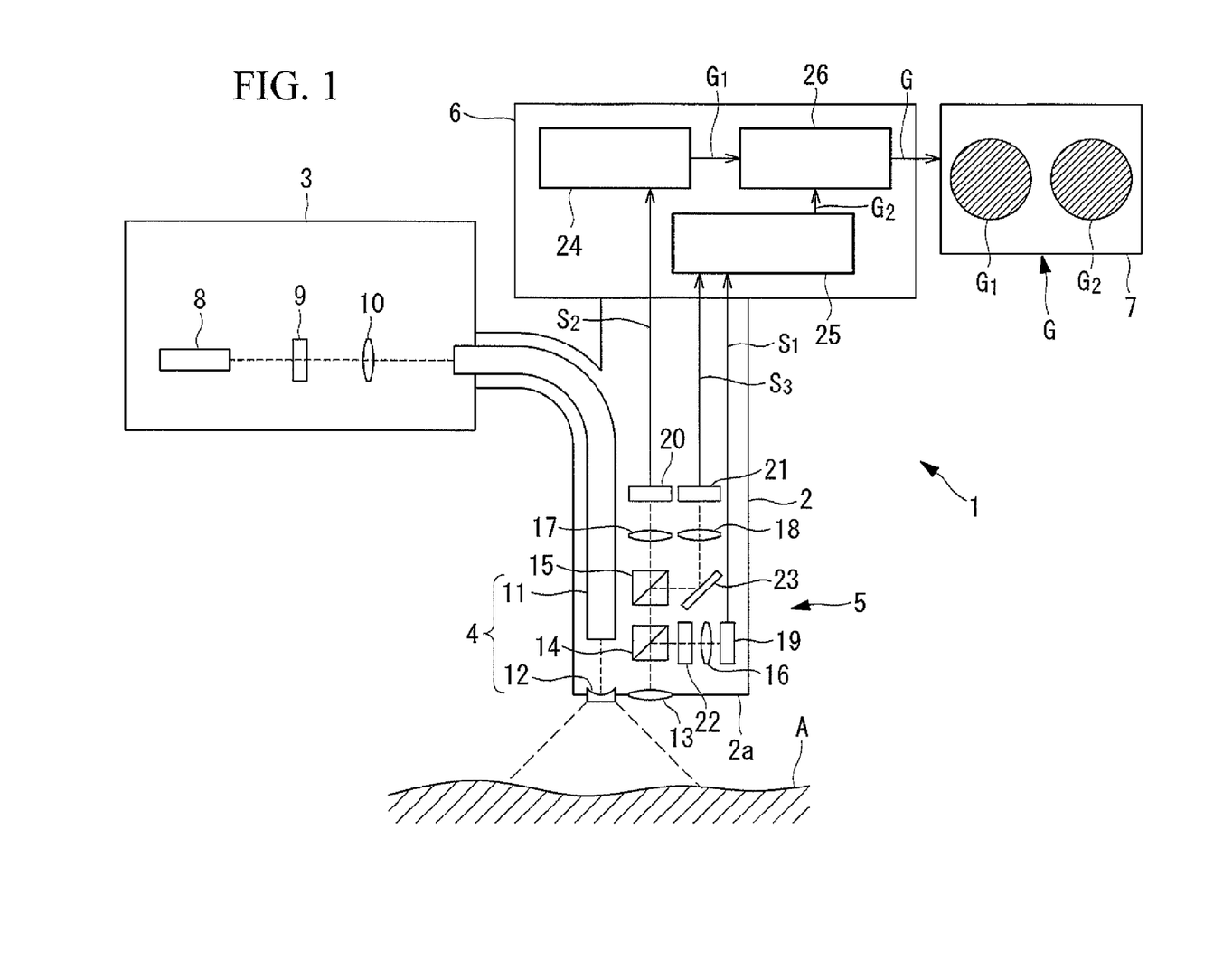
FIG. 1 is an overall configuration diagram showing a fluoroscopy apparatus according to an embodiment of the present invention.

The fluoroscopy apparatus 1 according to this embodiment is an endoscope apparatus. As shown in FIG. 1, the fluoroscopy apparatus 1 includes a long, thin inserted portion 2 that is inserted into a body, a light source (illumination portion) 3, an illumination unit (illumination portion) 4 that radiates illumination light coming from the light source 3 from the base end of the inserted portion 2 toward an observation target A, an image-acquisition unit 5 that is provided at the distal end of the inserted portion 2 and that acquires image information of biological tissue serving as the observation target A, an image processing unit 6 that is provided at the proximal end of the inserted portion 2 and that processes the image information acquired by the image-acquisition unit 5, and a monitor 7 that displays an image G processed by the image processing unit 6.

The light source 3 includes a xenon lamp 8, a filter 9 that extracts white light (a wavelength band of 400 to 740 nm) including excitation light from illumination light emitted from the xenon lamp 8, and a coupling lens 10 that focuses white the white light including excitation light extracted by the filter 9.

The illumination unit 4 is disposed substantially along the full length of the inserted portion 2 in the lengthwise direction. The illumination unit 4 includes a light guide fiber 11 that guides the white light including excitation light focused by the coupling lens 10, and an illumination optical system 12 that is provided at the distal end of the inserted portion 2 and that spreads the white light including excitation light guided by the light guide fiber 11 to irradiate the observation target A opposing a distal end face 2a of the inserted portion 2.

The image-acquisition unit 5 includes an objective lens 13 that collects returning light that returns from a specified observation region of the observation target A, a dichroic mirror (first splitting portion) 14 that reflects light having wavelengths longer than or equal to an excitation wavelength (excitation light and fluorescence) in the returning light collected by the objective lens 13 and transmits white light having wavelengths shorter than the excitation wavelength, a beam splitter 15 that further splits the white light transmitted through the dichroic mirror 14 into two, three focusing lenses (image-acquisition optical system) 16 to 18 that individually focus the fluorescence reflected by the dichroic mirror 14 and the two white light beams split by the beam splitter 15, and three image acquisition devices 19 to 21, such as CCDs, that individually acquire the fluorescence and two white light beams focused by the focusing lenses 16 to 18. In the figure, the reference sign 22 denotes an excitation-light cutting filter that blocks excitation light from the light reflected by the dichroic mirror 14, and the reference sign 23 denotes a mirror.

Figure 2A:
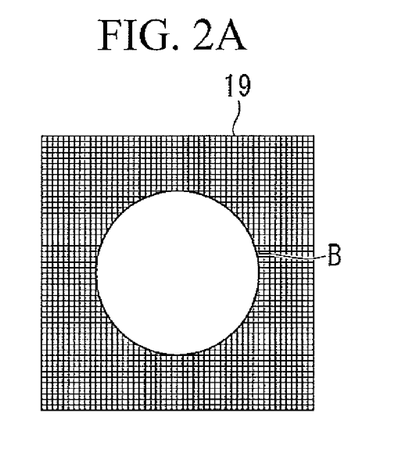
FIG. 2A is a schematic diagram showing a fluorescence image acquisition device of the fluoroscopy apparatus in FIG. 1.
Figure 2B:
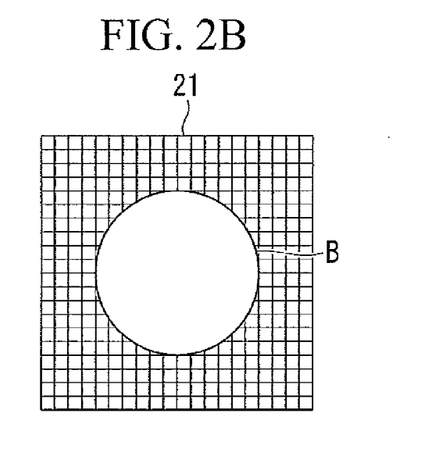
FIG. 2B is a schematic diagram showing a reference-light image acquisition device of the fluoroscopy apparatus in FIG. 1.

In this embodiment, the same types of lenses are used as the focusing lenses 16 to 18. As the image acquisition device 21 that acquires white light and the image acquisition device 19 that acquires fluorescence, image acquisition devices having different pixel densities are used, as shown in FIGS. 2A and 2B. In the figures, the reference sign B denotes the shapes of an object whose images are formed on the image-acquisition surfaces of the individual image acquisition devices 19 and 21.

The pixel density of the image acquisition device 21 is set to be sufficiently lower than the pixel density of the image acquisition devices 19 and 20. The image acquisition device 21 having a lower pixel density is used as the image acquisition device for acquiring reference image information $S_3$, and the image acquisition devices 19 and 20 having a higher pixel density are used as the image acquisition devices for acquiring fluorescence image information $S_1$ and white-light image information $S_2$, respectively.

The beam splitter 15 is configured to split white light by such a ratio that the amount of light directed to the image acquisition device 21 for acquiring the reference image information $S_3$ is sufficiently less than the amount of light directed to the image acquisition device 20 for acquiring the white-light image information $S_2$.

The image processing unit 6 includes a reflected-light-image generating unit 24 that generates a reflected-light image $G_1$ from the white-light image information $S_2$ acquired by the image acquisition device 20, a corrected-fluorescence-image generating unit 25 that generates a corrected fluorescence image $G_2$ on the basis of the fluorescence image information $S_1$ acquired by the image acquisition device 19 and the reference image information $S_3$ acquired by the image acquisition device 21, and an image-combining unit 26 that combines the reflected-light image $G_1$ and the corrected fluorescence image $G_2$ to generate an image G.

The corrected-fluorescence-image generating unit 25 processes the reference image information $S_3$ acquired at a low resolution into reference image information $S_3$ having the same number of pixels as the fluorescence image information $S_1$ and then divides the fluorescence image information $S_1$ by the reference image information $S_3$ pixelwise, thereby generating the corrected fluorescence image $G_2$.

The image-combining unit 26 generates an image G and outputs it to the monitor 7 so that, for example, the reflected-light image $G_1$ and the corrected fluorescence image $G_2$ are arranged side by side and displayed simultaneously on the monitor 7.

The operation of the thus-configured fluoroscopy apparatus 1 according to this embodiment will be described below.

In order to observe biological tissue inside a body, serving as the observation target A, by using the fluoroscopy apparatus 1 according to this embodiment, the inserted portion 2 is inserted into the body, and the distal end face 2a of the inserted portion 2 is placed opposite the observation target A. Then, the light source 3 is operated to generate white light including excitation light, which enters the light guide fiber 11 through the coupling lens 10. The white light including excitation light, guided through the light guide fiber 11 to the distal end of the inserted portion 2, is spread by the illumination optical system 12 at the distal end of the inserted portion 2 and irradiates the observation target A.

A fluorescent material contained inside the observation target A is excited by the excitation light to generate fluorescence, and white light is reflected at the surface of the observation target A. The fluorescence and reflected white light (returning light) return to the distal end face 2a of the inserted portion 2 from the observation target A, and returning light emitted from a part of the observation region thereof is collected by the objective lens 13.

The returning light collected by the objective lens 13 is split on the basis of wavelength by the dichroic mirror 14, and returning light at and above the excitation wavelength, i.e., excitation light and fluorescence, is reflected by the dichroic mirror 14. Then, the excitation light is removed by the excitation-light cutting filter 22, so that only the fluorescence is focused by the focusing lens 16 and acquired by the image acquisition device 19 as the fluorescence image information $S_1$.

Of the returning light collected by the objective lens 13, the white light having wavelengths shorter than the excitation wavelength is split into two by the beam splitter 15, and one of the white light beams is focused by the focusing lens 17 and acquired by the image acquisition device 20 as the white-light image information $S_2$, and the other white light beam is focused by the focusing lens 18 and acquired by the image acquisition device 21 as the reference image information $S_3$.

The image information $S_1$ to $S_3$ acquired individually by the image acquisition devices 19 to 21 are sent to the image processing unit 6, where the white-light image information $S_2$ is input to the reflected-light-image generating unit 24 and the reflected-light image $G_1$ is generated. On the other hand, the fluorescence image information $S_1$ and the reference image information $S_3$ are input to the corrected-fluorescence-image generating unit 25, where the fluorescence image information $S_1$ is divided by the reference image information $S_3$ pixelwise to generate the corrected fluorescence image $G_2$.

In this case, the illumination light is spread by the illumination optical system 12, so that different regions of the observation target A are irradiated under different conditions of angle and distance, and thus the irradiation intensity of excitation light varies among regions. Therefore, the fluorescence image information $S_1$ includes intensity variation that depends on the distance and angle of the illumination light. That is, even if the fluorescent material is contained uniformly in the entire region, the intensity of fluorescence $L_1$ that is actually produced varies depending on the angle and distance of the illumination light.

On the other hand, the reference image information $S_3$ is acquired with the same conditions of irradiation with the illumination light and in the same observation region as the fluorescence image information $S_1$. Therefore, as information indicating intensity variation attributable to the distance and angle of the illumination light, the reference image information $S_3$ includes information equivalent to that included in the fluorescence image information $S_1$. Furthermore, in this embodiment, since the reference image information $S_3$ is acquired by the image acquisition device 21 having a sufficiently low pixel density, the resolution is reduced, so that information regarding the surface condition of the observation target A is reduced.

As described above, with the fluoroscopy apparatus 1 according to this embodiment, even if regions of blood vessel structures or various other characteristic shaped portions exist on the surface of the observation target A, information about such regions of characteristic shaped portions is removed from the reference image information $S_3$, and information of intensity variation based on the angle and distance of the illumination light is maintained. As a result, by correcting the fluorescence image information $S_1$ by using the thus-acquired reference image information $S_3$, it is possible to acquire the corrected fluorescence image $G_2$ having a high quantitativeness, corrected as if conditions of irradiation with the excitation light were uniform regardless of the angle and distance of the excitation light.

With the fluoroscopy apparatus 1 according to this embodiment, simply by acquiring an image with the image acquisition device 21 having a low pixel density, it is possible to acquire the reference image information $S_3$ including information of intensity variation based on the angle and distance of the illumination light and having a low resolution. Therefore, special optical devices or calculation processing are not needed, so that an advantage is afforded in that it is possible to quickly acquire the corrected fluorescence image $G_2$ having a high quantitativeness with a simple configuration.

Figure 3A:
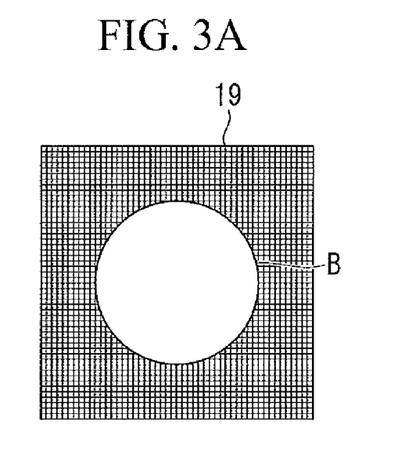
FIG. 3A is a schematic diagram showing a fluorescence image acquisition device in a first modification of the fluoroscopy apparatus in FIG. 1.
Figure 3B:
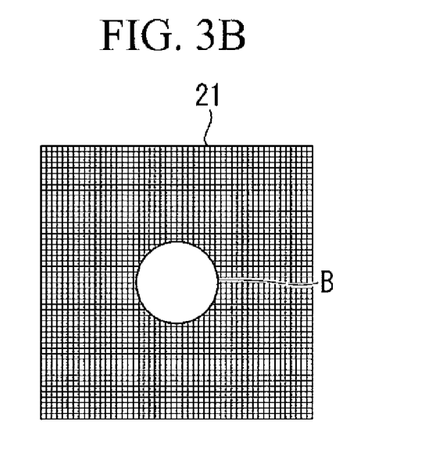
FIG. 3B is a schematic diagram showing a reference-light image acquisition device in the first modification of the fluoroscopy apparatus in FIG. 1.
Figure 4A:
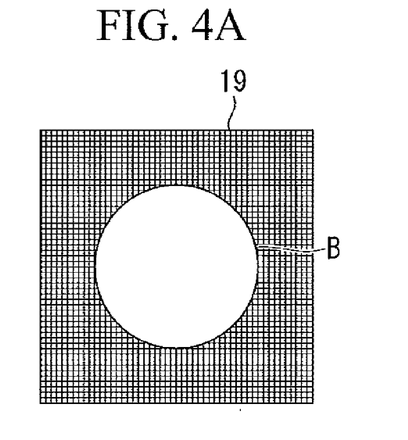
FIG. 4A is a schematic diagram showing a fluorescence image acquisition device in a second modification of the fluoroscopy apparatus in FIG. 1.
Figure 4B:
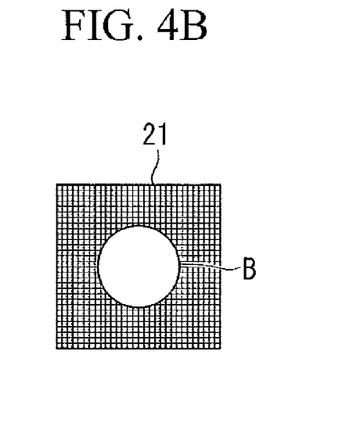
FIG. 4B is a schematic diagram showing a reference-light image acquisition device in the second modification of the fluoroscopy apparatus in FIG. 1.

In this embodiment, the image acquisition device 21 having a low pixel density is used as the image acquisition device 21 for acquiring the reference image information $S_3$. Alternatively, as the image acquisition devices 21, it is possible to use an image acquisition device having a pixel density equivalent to that of the image acquisition device 20 for acquiring the white-light image information $S_2$ and, as the focusing lens 18, to use a focusing lens with a smaller image-forming magnification than the other focusing lens 17 for white light. Also in this case, as shown in FIGS. 3A and 3B, the reference image information $S_3$ with a low image-forming magnification is acquired, so that similar correction can be performed. Alternatively, as shown in FIGS. 4A and 4B, an image acquisition device having the same pixel density and a smaller number of pixels may be used as the image acquisition device 21 for acquiring the reference image information $S_3$.

The image acquisition device 21 for acquiring the reference image information $S_3$ may perform pixel binning. This substantially reduces the pixel density, so that it is possible to acquire a corrected fluorescence image similarly to the case described above.

That is, the pixel density of the image acquisition device 21 and the image-forming magnification of the focusing lens 18 should be chosen so that the product of the image-forming magnification of the focusing lens 16 for acquiring the fluorescence image information $S_1$ and the effective pixel density of the image acquisition device 19 is sufficiently greater than the product of the image-forming magnification of the focusing lens 18 for acquiring the reference image information $S_3$ and the effective pixel density of the image acquisition device 21.

Although the acquired fluorescence image information $S_1$ is divided by the reference image information $S_3$ pixelwise in this embodiment, alternatively, other types of correction processing, such as subtraction processing, may be performed.

Figure 5:
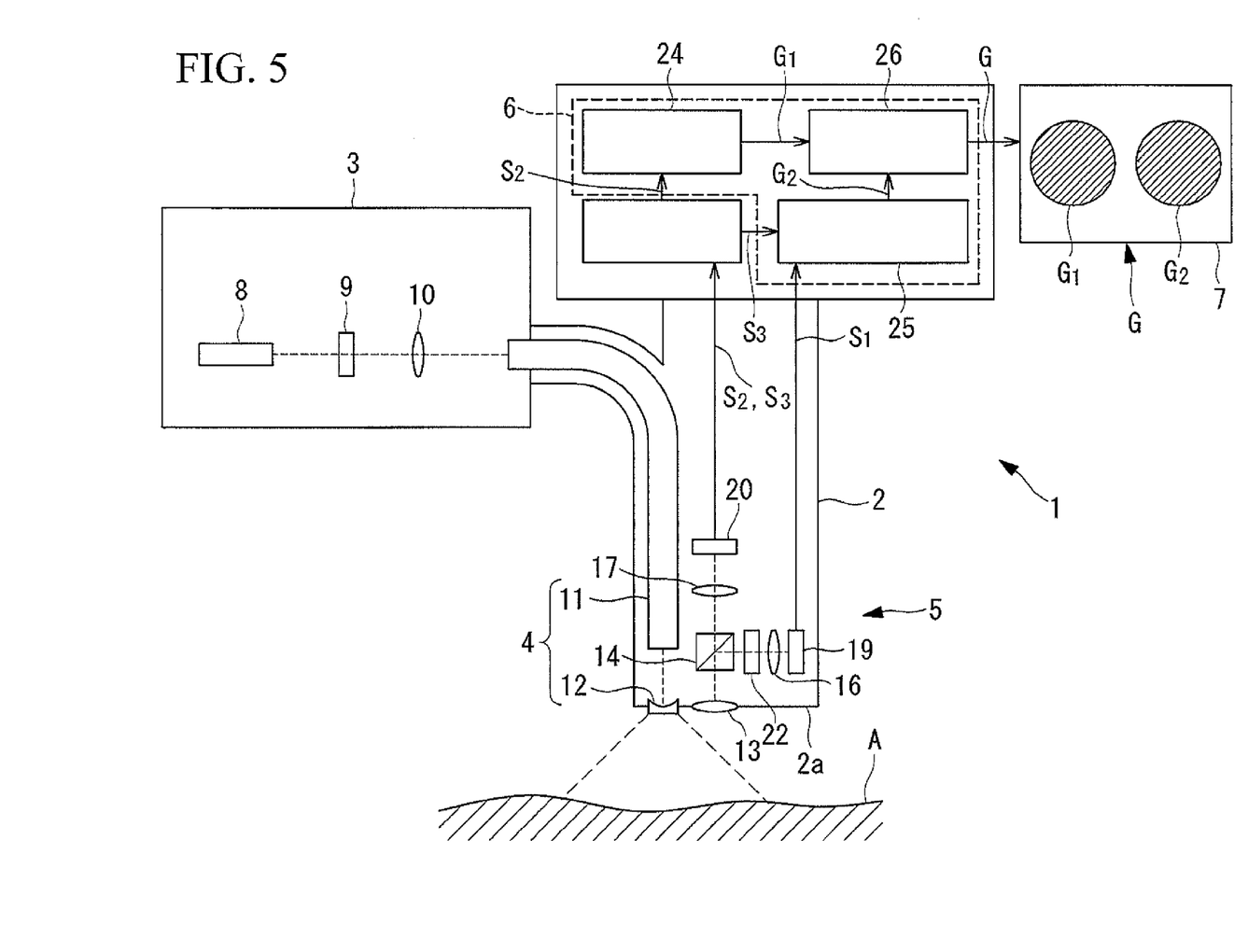
FIG. 5 is an overall configuration diagram showing a third modification of the fluoroscopy apparatus in FIG. 1.

Although this embodiment is described in the context of a case where image acquisition device 20 for acquiring the white-light image information $S_2$ and the image acquisition device 21 for acquiring the reference image information $S_3$ are provided separately, alternatively, as shown in FIG. 5, the beam splitter 15 may be omitted, and both the white-light image information $S_2$ and the reference image information $S_3$ may be acquired with the single image acquisition device 20.

Figure 6:
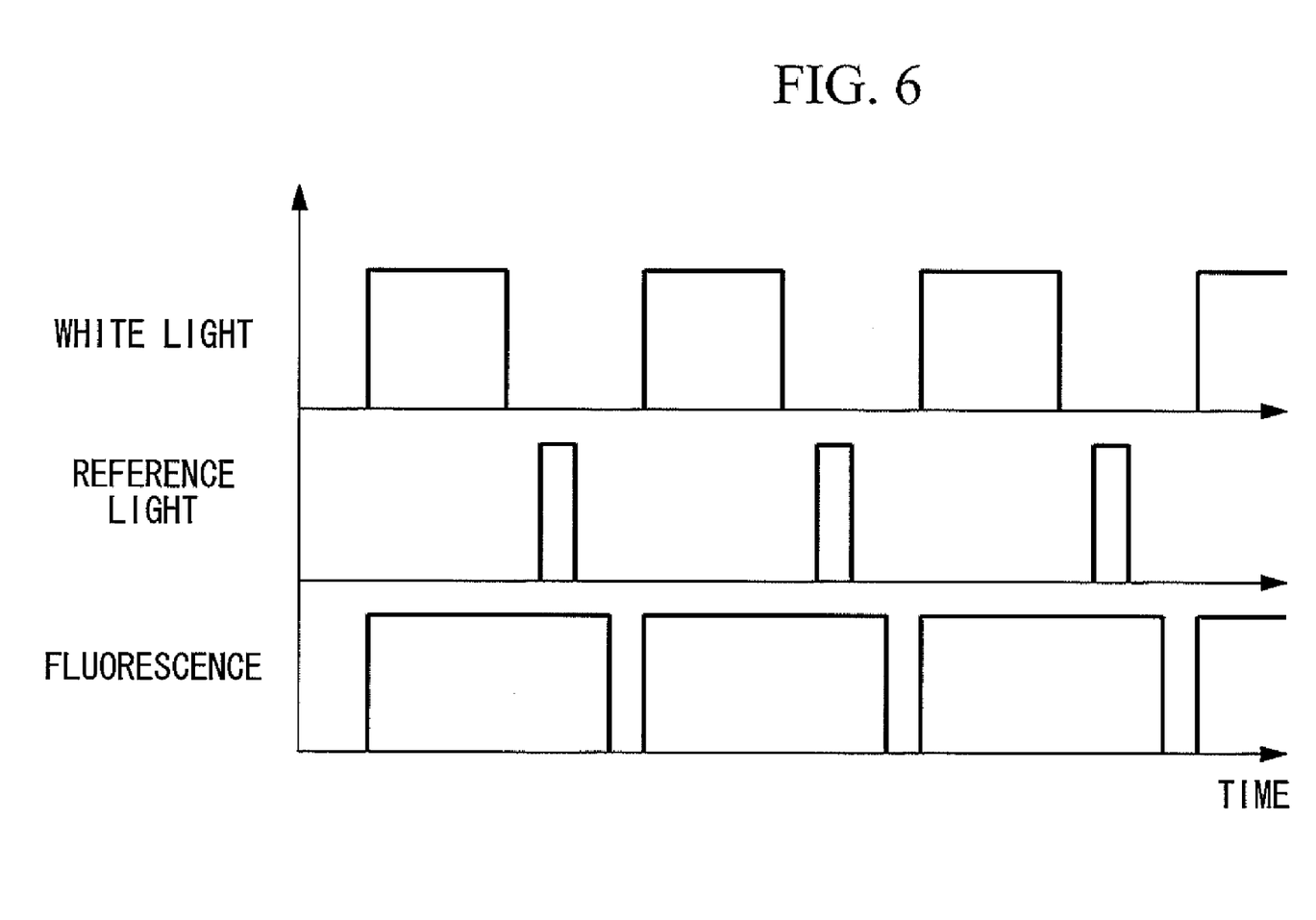
FIG. 6 is a timing chart showing timing at which image information is acquired by the fluoroscopy apparatus in FIG. 5.

In this case, as shown in FIGS. 5 and 6, the white-light image information $S_2$ and the reference image information $S_3$ may be acquired alternately by time division under the control of a switching controller 27 from image information acquired by the image acquisition device 20. The reference image information $S_3$ may be constructed by controlling the timing at which pixel information of the acquired white-light image information $S_2$ is read out so that image information is read out at intervals of one or more pixels: in the case of the example shown in FIG. 7, image information is read out at intervals of five pixels, as indicated by hatching.

Figure 7:
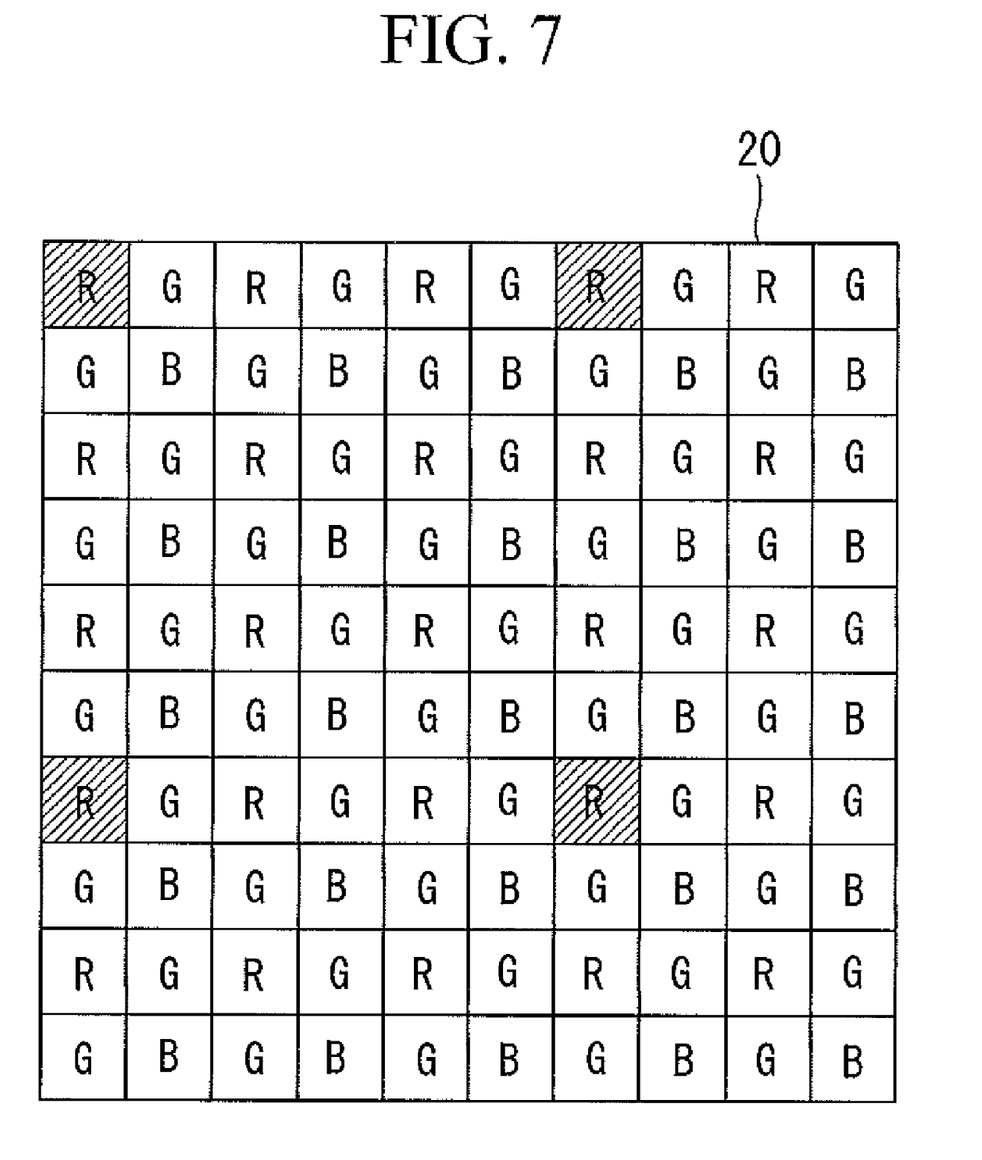
FIG. 7 is a schematic diagram of an image acquisition device, which serves to explain timing at which reference image information is read out by the fluoroscopy apparatus in FIG. 5.

Although only R (red) signals are read in the example shown in FIG. 7, alternatively, G (green) signals or B (blue) signals may be read.

The pixel binning by the image acquisition device 20 may be switched on and off alternately so that the white-light image information $S_2$ and the reference image information $S_3$ are acquired alternately in a time division manner.

Although the embodiments described above are described in the context of examples where the fluoroscopy apparatus 1 is an endoscope, without limitation to the embodiments, application to other arbitrary types of the fluoroscopy apparatus 1 is possible.

What is claimed is:

1. A fluoroscopy apparatus comprising:
an illumination portion that irradiates an observation target with illumination light including excitation light;
a fluorescence image acquisition device that acquires fluorescence emitted from a specified observation region of the observation target to acquire a fluorescence image;
a fluorescence image-acquisition optical system that forms an image of the observation target using the fluorescence on an image-acquisition surface of the fluorescence image acquisition device;
a reference-light image acquisition device that acquires returning light returning from the observation region to acquire a reference image;
a reference-light image-acquisition optical system that forms an image of the observation target using the returning light on an image-acquisition surface of the reference-light image acquisition device; and
an image correction section that corrects the fluorescence image acquired by the fluorescence image acquisition device by using the reference image acquired by the reference-light image acquisition device,
wherein the product of an effective pixel density of the reference-light image acquisition device and an image-forming magnification of the reference-light image-acquisition optical system is less than the product of the pixel density of the fluorescence image acquisition device and an image-forming magnification of the fluorescence image-acquisition optical system.

2. A fluoroscopy apparatus according to claim 1, wherein the image correction section divides the fluorescence image by the reference image.

3. A fluoroscopy apparatus according to claim 1, wherein the reference-light image acquisition device acquires the reference image at a pixel density lower than the actual pixel density by pixel binning.

4. A fluoroscopy apparatus according to claim 3, wherein the reference-light image acquisition device acquires the reference image acquired with pixel binning and a returning-light image acquired without pixel binning in a time division manner by switching pixel binning on and off.

5. A fluoroscopy apparatus according to claim 1 comprising:
a light-collecting lens that collects returning light returning from the observation target after the illumination portion irradiates the observation target simultaneously with white light and excitation light as illumination light;
a first splitting portion that splits the returning light collected by the light-collecting lens into fluorescence and white light;
a second splitting portion that further splits the white light split by the first splitting portion;
a white-light image-acquisition optical system that focuses one of the white light beams split by the second splitting portion; and
a white-light image acquisition device having an image-acquisition surface at a focal position of the white-light image-acquisition optical system,
the fluorescence split by the first splitting portion is guided to the fluorescence image acquisition device, and
the other white light beam split by the second splitting portion is guided to the reference-light image acquisition device via the reference-light image-acquisition optical system.

6. A fluoroscopy apparatus comprising:
an illumination portion that irradiates an observation target with illumination light including excitation light;
a fluorescence image acquisition device that acquires fluorescence emitted from a specified observation region of the observation target to acquire a fluorescence image;
a fluorescence image-acquisition optical system that forms an image of the observation target using the fluorescence on an image-acquisition surface of the fluorescence image acquisition device;
a returning-light image acquisition device that acquires returning light returning from the observation region;
a returning-light image-acquisition optical system that forms an image of the observation target using the returning light on an image-acquisition surface of the returning- light image acquisition device;
a reference-image generating unit that generates a reference image by decimating pixels of a returning-light image acquired by the returning-light image acquisition device; and
an image correction section that corrects the fluorescence image acquired by the fluorescence image acquisition device by using the reference image generated by the reference-image generating unit.

7. A fluoroscopy apparatus according to claim 6, wherein the reference-image generating unit generates the reference image by reading out pixel information at intervals of one or more pixels of the returning-light image acquired by the returning-light image acquisition device.

8. A fluoroscopy apparatus according to claim 7, wherein the reference-image generating unit controls the timing at which the returning-light image is read out when generating the reference image.

9. A fluoroscopy apparatus according to claim 8, wherein the reference-image generating unit switches the timing at which the returning-light image is read out to generate, in a time division manner, the reference image at delayed readout timing and the returning-light image at advanced readout timing.

* * * * *